(12) United States Patent
Kwong

(10) Patent No.: US 7,150,061 B2
(45) Date of Patent: Dec. 19, 2006

(54) ELECTRIC TOOTHBRUSH

(76) Inventor: Mei Ki Kwong, Flat 2, 9/F, Hung Fuk House, 47 Fuk Wah Street, Sham Shui Po, Kowloon, Hong Kong (CN)

( * ) Notice: Subject to any disclaimer, the term of this patent is extended or adjusted under 35 U.S.C. 154(b) by 591 days.

(21) Appl. No.: 10/690,323

(22) Filed: Oct. 21, 2003

(65) Prior Publication Data

US 2005/0081315 A1 Apr. 21, 2005

(30) Foreign Application Priority Data

Mar. 20, 2003 (CN) ................ 03 2 24615

(51) Int. Cl.
*A61C 17/22* (2006.01)
(52) U.S. Cl. .............. 15/22.1; 15/28; 15/22.4
(58) Field of Classification Search ........ 15/22.1, 15/28, 22.4, 22.2; 433/114, 118, 131, 216
See application file for complete search history.

(56) References Cited

U.S. PATENT DOCUMENTS

| | | | |
|---|---|---|---|
| 1,833,916 A * | 12/1931 | Shaler | 30/45 |
| 3,978,852 A * | 9/1976 | Annoni | 601/142 |
| 4,149,291 A | 4/1979 | Stoltz | |
| 4,225,994 A | 10/1980 | Stoltz | |
| 5,253,382 A * | 10/1993 | Beny | 15/22.1 |
| 2004/0177458 A1* | 9/2004 | Chan et al. | 15/22.1 |
| 2005/0055784 A1* | 3/2005 | Wong | 15/22.1 |
| 2006/0010622 A1* | 1/2006 | Naruse et al. | 15/22.1 |

* cited by examiner

*Primary Examiner*—Gary K. Graham
(74) *Attorney, Agent, or Firm*—Alix, Yale & Ristas, LLP

(57) ABSTRACT

An electric toothbrush has a neck extending in a longitudinal direction, a head at a remote end of the neck, a handle at a proximal end of the neck, an electric motor located within the handle, and a tuft block mounted to the head in a manner allowing pivotal oscillation about a tuft block axis that is normal to the longitudinal direction of the neck. A primary rocker arm extends longitudinally within the handle and/or neck and pivots about a primary rocker arm axis that is parallel to the tuft block axis. A proximal end of the primary rocker arm is driven by the electric motor. A secondary rocker arm extends longitudinally within the neck and pivots about a secondary rocker arm axis that is parallel to the tuft block axis. A distal end of the secondary rocker arm drives the tuft block and a proximal end of the secondary rocker arm is driven by the primary rocker arm.

6 Claims, 5 Drawing Sheets

ELECTRIC TOOTHBRUSH

BACKGROUND OF THE INVENTION

The present invention relates to electric toothbrushes. More particularly, although not exclusively, the invention relates to an electric toothbrush head having a tuft block that oscillates about a pivot axis.

Many electric toothbrushes have been proposed with rotating or pivotally oscillating bristle heads. Many of these suffer from complexity of design, cleaning-inefficiency and general inefficiency in operation.

OBJECT OF THE INVENTION

It is an object of the present invention to overcome or substantially ameliorate the above disadvantage and/or more generally to provide an improved electric toothbrush.

DISCLOSURE OF THE INVENTION

There is disclosed here in an electric toothbrush, comprising:
  a neck extending in a longitudinal direction of the toothbrush,
  a head at a remote end of the neck,
  a handle at a proximal end of the neck,
  an electric motor located within the handle,
  a tuft block mounted to the head in a manner allowing pivotal oscillation thereof about a tuft block axis substantially normal to the longitudinal direction of the neck,
  a primary rocker arm extending longitudinally within the handle and/or neck and pivoting about a primary rocker arm axis substantially parallel to the tuft block axis, a proximal end of the primary rocker arm being driven by the electric motor, and
  a secondary rocker arm extending longitudinally within the neck and pivoting about a secondary rocker arm axis substantially parallel to the tuft block axis, a distal end of the secondary rocker arm driving the tuft block and a proximal end of the secondary rocker arm being driven by the primary rocker arm.

Preferably the tuft block comprises a recess socket and the secondary rocker arm has at its distal end a ball received within the recess socket.

Preferably the recess socket is a slot extending in a direction substantially parallel to the pivot axis of the top block.

Preferably the electric toothbrush further comprises a coupling between the motor and the primary rocker arm, the coupling having an eccentric boss received within a slot at the proximal end of the primary rocker arm.

Preferably the electric toothbrush further comprises a flexible seal surrounding the primary rocker arm.

Preferably the primary and secondary rocker arms are interconnected by a pivot pin.

Definition

As used herein, the term "electric motor" is intended to encompass rotary devices including an armature, a stator, a winding and an output shaft, or other devices including vibrating transformers, solenoids other devices that convert electric energy into mechanical output movement.

BRIEF DESCRIPTION OF THE DRAWINGS

A preferred form of the present invention will now be described by way of example with reference to the accompanying drawings, wherein.

DESCRIPTION OF THE PREFERRED EMBODIMENT

Figure 1A:
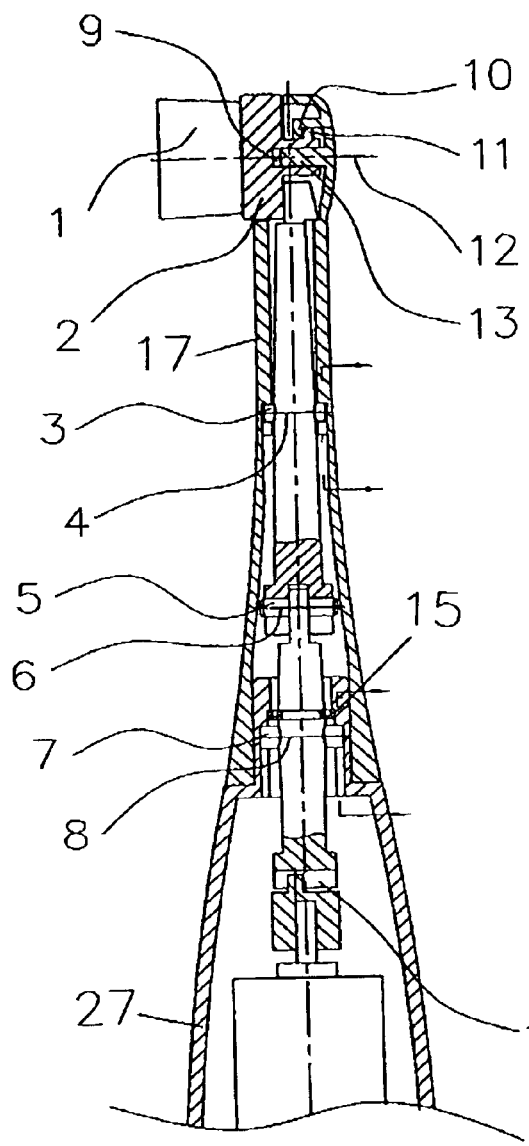
FIG. 1a is a schematic cross-sectional side elevation of a toothbrush head and handle forward part.
Figure 1B:
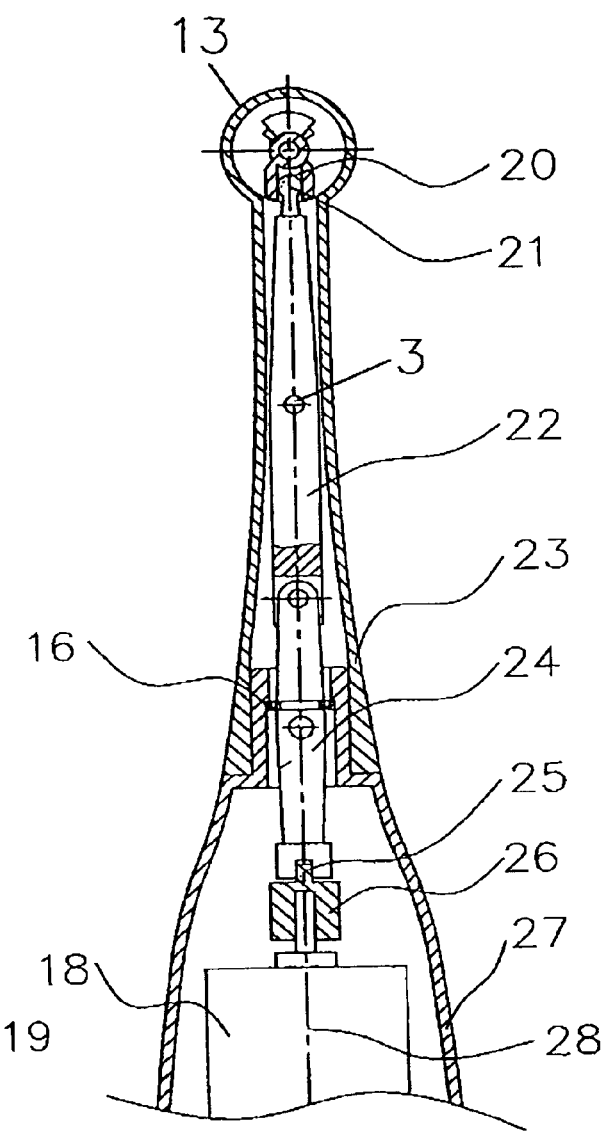
FIG. 1b is a schematic cross-sectional front elevation of the toothbrush head and handle forward part of FIG. 1a,
  FIG. 2a is a schematic cross-sectional front elevation of the toothbrush head and handle forward part with internal components at one angular extremity.
Figures 2A, 2B:
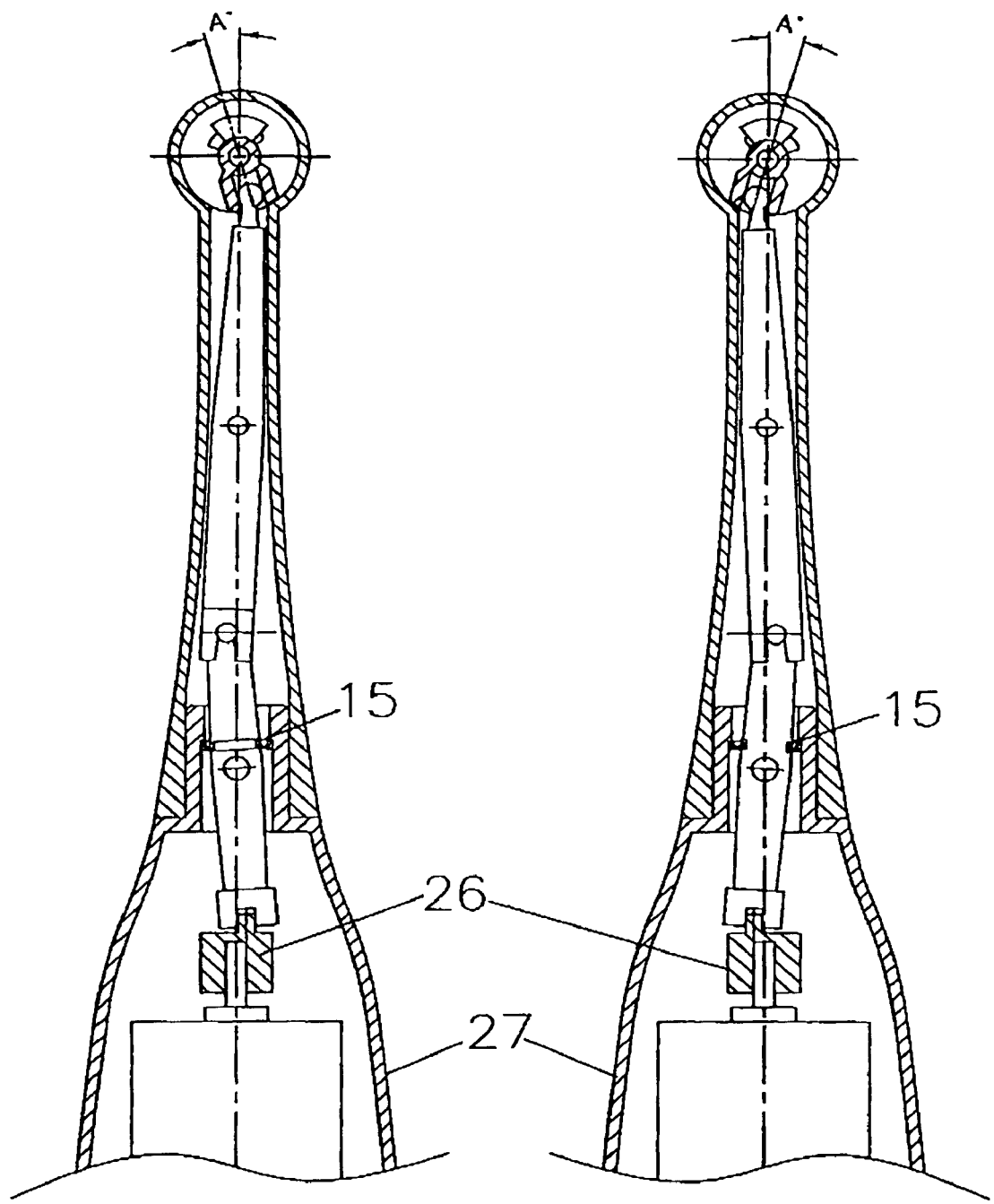
FIG. 2b is a schematic cross-sectional front elevation of the toothbrush head and handle forward part with internal components at and opposite angular extremity.
Figure 3C:
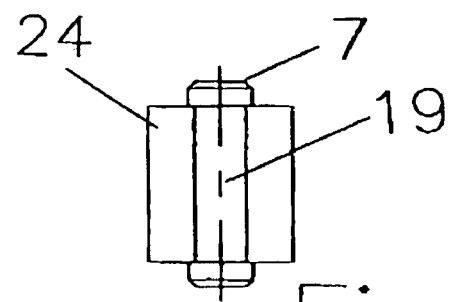
FIG. 3c is a schematic inverted plan view of the primary rocker arm of FIG. 3a and 3b.
Figure 3A:
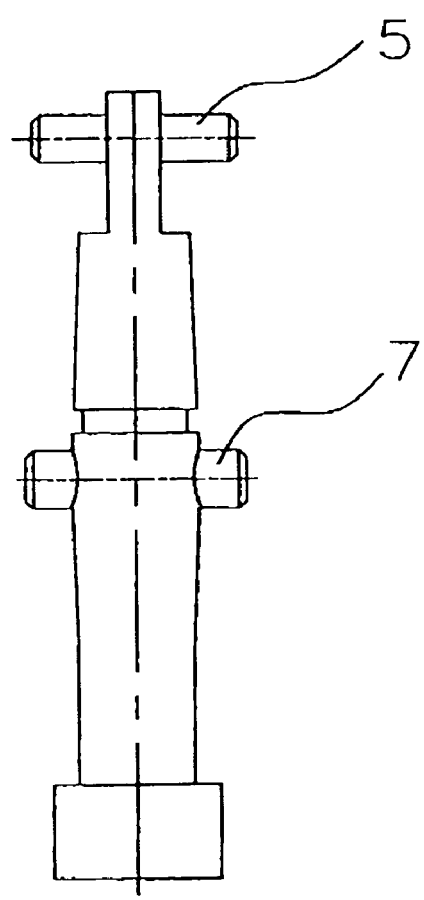
FIG. 3a is a schematic side elevation of a primary rocker arm forming part of the toothbrush.
Figure 3B:
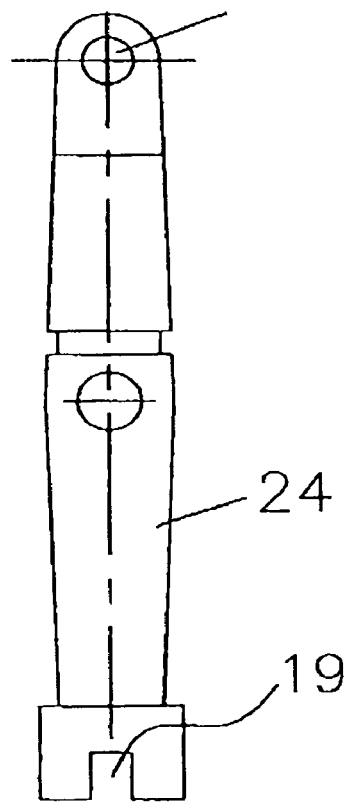
FIG. 3b is a schematic front elevation of the rocker arm of FIG. 3a comet
Figure 4:
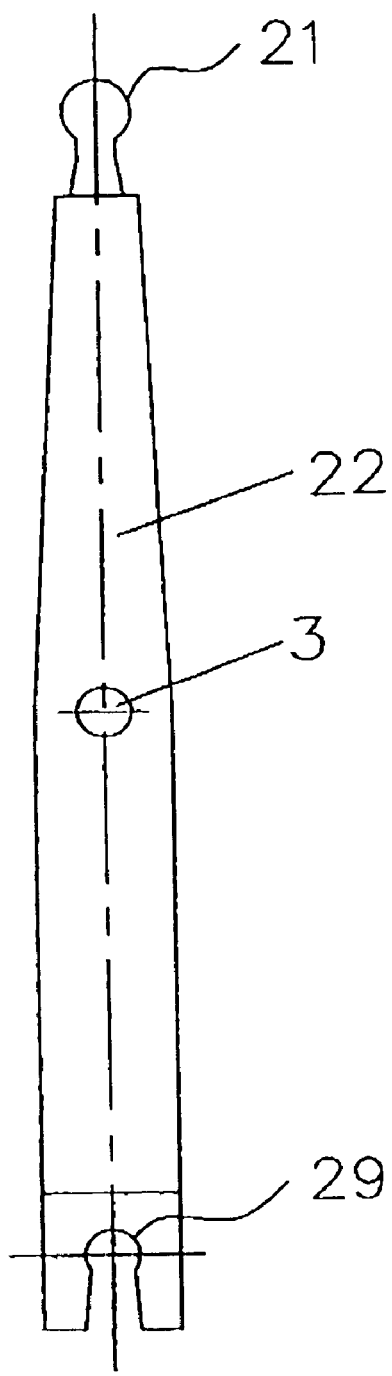
FIG. 4 is a schematic front elevation of a secondary rocker arm.

In the accompanying drawings there is depicted schematically an electric toothbrush comprising a handle 27 to which there is attached a replaceable neck 17 at the end of which there is a head 13. A tuft block 2 having bristles 1 is mounted upon a pin 9 to pivot about tuft block pivot axis 12. Pivot axis 12 extends normally to the longitudinal axis 28 of the toothbrush. To maintain the tuft block 2 upon pivot pin 9, there is a key 11 that fits behind a flange 10 as shown in FIGS. 1a and 1b.

The neck and handle as well as the tuft block and internal components are typically formed as plastics mouldings.

Within the handle 27 there is an electric motor 18 having a coupling 26 mounted upon it's output shaft. The coupling 26 has an eccentric boss 25 projecting therefrom.

There is a primary rocker arm 24 mounted at the forward end of the handle 27 at a position about which the neck 17 is attached thereto. The primary rocker arm has a pivot pin 7 by which the arm is mounted within the handle 27. The proximal end of the primary rocker arm has a transverse Blot 19 into which the eccentric boon 25 is received. Just forward of the pivot pin 7 there is a flexible seal 15 preventing ingress of liquid to the handle interior.

At the distal end of the primary rocker arm there is another pivot pin 5 that is snap-engaged within a pin socket 29 at the proximal end of a secondary rocker arm 22.

The secondary rocker arm 22 is mounted upon a pivot pin 3 internally of the neck 17 and has a ball 21 at its distal end. The ball 21 is received within a recess socket 20 in the tuft block 2. Recess socket 20 takes the form of a slot having a width that is approximately equal to the size of the ball 21.

Figure 5:
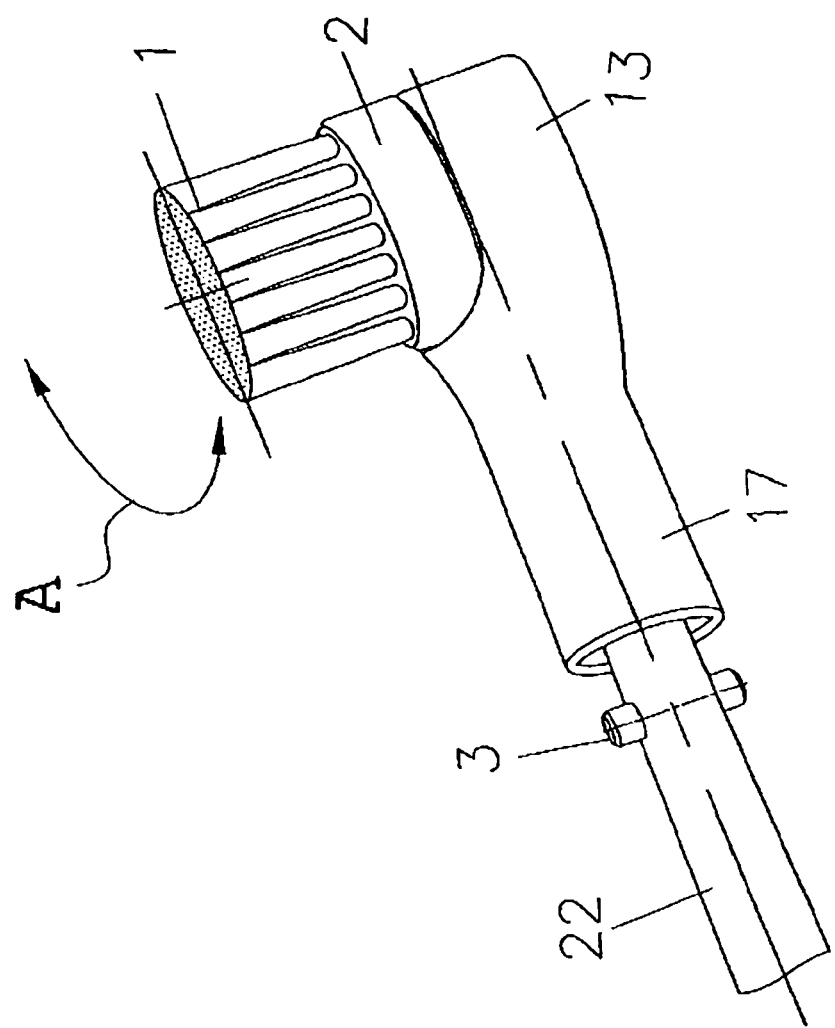
FIG. 5 is a schematic perspective illustration of the toothbrush head shown in FIGS. 1a, 1b, 2a and 2b.

In use, the electric motor 18 is activated by a switch (not shown) that receives power from a battery within the handle 27. The coupling 26 rotates in such a manner that the eccentric boss 25 orbits the longitudinal axis 28. As the boss 25 is received within the slot 19, the primary rocker arm will pivot back and forth about axis 8 of pivot pin 7. Because the distal end of primary rocker arm 24 is engaged with the proximal end of the secondary rocker arm 22, the secondary rocker arm will pivot back and forth about axis 4 of pivot pin 3. As a result, the ball 21 will move back and forth to thereby cause pivotal oscillation of the tuft block 2 as shown by arrow A in FIG. 5.

It should be appreciated that modifications and alterations obvious to those skilled in the art are not to be considered as beyond the scope of the present invention. For example, a seal like seal 16 right be provided adjacent to the pivot pin 3 of the secondary rocker arm. Furthermore, instead of providing a standard electric motor of the type depicted in the drawings, a vibrating transformer, oscillating solenoid or other device for converting electric energy into output movement might be used.

The invention claimed is:

1. An electric toothbrush, comprising:
   a neck extending in a longitudinal direction of the toothbrush,
   a head at a remote end of the neck,
   a handle at a proximal end of the neck,
   an electric motor located within the handle,
   a tuft block mounted to the head in a manner allowing pivotal oscillation thereof about a tuft block axis substantially normal to the longitudinal direction of the neck,
   a primary rocker arm extending longitudinally within the handle and/or neck and pivoting about a primary rocker arm axis substantially parallel to the tuft block axis, a proximal end of the primary rocker arm being driven by the electric motor, and
   a secondary rocker arm extending longitudinally within the neck and pivoting about a secondary rocker arm axis substantially parallel to the tuft block axis, a distal end of the secondary rocker arm driving the tuft block and a proximal end of the secondary rocker arm being driven by the primary rocker arm.

2. The electric toothbrush of claim 1 wherein the tuft block comprises a recess socket and the secondary rocker arm has at its distal end a ball received within the recess socket.

3. Electric toothbrush of claim 2 wherein the recess socket is a slot extending in a direction substantially parallel to the pivot axis of the top block.

4. The electric toothbrush of claim 1 further comprising a coupling between the motor and the primary rocker arm, the coupling having an eccentric boss received within a slot at the proximal end of the primary rocker arm.

5. The electric toothbrush of claim 1 further comprising a flexible seal surrounding the primary rocker arm.

6. The electric toothbrush of claim 1 wherein the primary and secondary rocker arms are interconnected by a pivot pin.

* * * * *

UNITED STATES PATENT AND TRADEMARK OFFICE
CERTIFICATE OF CORRECTION

| | | |
|---|---|---|
| PATENT NO. | : 7,150,061 B2 | Page 1 of 1 |
| APPLICATION NO. | : 10/690323 | |
| DATED | : December 19, 2006 | |
| INVENTOR(S) | : Kwong | |

It is certified that error appears in the above-identified patent and that said Letters Patent is hereby corrected as shown below:

<u>Column 4</u>:
Line 16, delete "top" and substitute --tuft--.

Signed and Sealed this

Fifth Day of June, 2007

JON W. DUDAS
*Director of the United States Patent and Trademark Office*